US009999768B2

(12) United States Patent
Gelfand et al.

(10) Patent No.: US 9,999,768 B2
(45) Date of Patent: *Jun. 19, 2018

(54) RESPIRATORY RECTIFICATION (75) Inventors: Mark Gelfand, New York, NY (US); Kristofer J. James, Eagan, MN (US); Randy W. Westlund, River Falls, WI (US); Antonis Panteleon, Edina, MN (US); Todd P. Goblish, Maple Grove, MN (US); Mark C. Lynn, St. Anthony, MN (US)

(73) Assignee: Respicardia, Inc., Minnetonka, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/529,770

(22) Filed: Jun. 21, 2012

(65) Prior Publication Data
US 2013/0158625 A1    Jun. 20, 2013

Related U.S. Application Data (63) Continuation of application No. 12/557,084, filed on Sep. 10, 2009, now Pat. No. 8,233,987.

(51) Int. Cl.
*A61N 1/36*    (2006.01)

(52) U.S. Cl.
CPC .......... *A61N 1/3601* (2013.01); *A61N 1/3611* (2013.01); *A61N 1/36171* (2013.01)

(58) Field of Classification Search
CPC ................................................. A61N 1/3601
See application file for complete search history.

(56) References Cited

U.S. PATENT DOCUMENTS

| | | |
|---|---|---|
| 4,129,125 A | 12/1978 | Lester et al. |
| 4,702,253 A | 10/1987 | Nappholz et al. |
| 4,827,935 A | 5/1989 | Geddes et al. |
| 4,830,008 A | 5/1989 | Meer |
| 5,002,067 A | 3/1991 | Berthelsen et al. |
| 5,056,519 A | 10/1991 | Vince |
| 5,146,918 A | 9/1992 | Kallok et al. |
| 5,170,802 A | 12/1992 | Mehra |
| 5,199,428 A | 4/1993 | Obel et al. |
| 5,265,604 A | 11/1993 | Vince |
| 5,330,507 A | 7/1994 | Schwartz |
| 5,423,865 A | 6/1995 | Bowald et al. |
| 5,483,969 A | 6/1995 | Bowald et al. |

(Continued)

FOREIGN PATENT DOCUMENTS

| | | |
|---|---|---|
| DE | 10103288 A1 | 8/2002 |
| WO | 01/41868 A | 6/2001 |

(Continued)

OTHER PUBLICATIONS

Chinese Application dated Jun. 13, 2016 for corresponding Chinese Application No. 201080040438.2, filed Mar. 12, 2012.

(Continued)

*Primary Examiner* — Kennedy Schaetzle
(74) *Attorney, Agent, or Firm* — Frank P. Piskolich (57) ABSTRACT

A means for treating breathing disorders by stimulating respiratory muscles or nerves to entrain respiratory systems while leaving respiratory drive intact. Embodiments of the invention employ frequency analysis to determine if appropriate stimulation energy is being applied.

13 Claims, 6 Drawing Sheets

(56) References Cited

U.S. PATENT DOCUMENTS

| | | | |
|---|---|---|---|
| 5,485,851 A | 1/1996 | Erickson | |
| 5,524,632 A | 6/1996 | Stein et al. | |
| 5,578,061 A | 11/1996 | Stroetmann et al. | |
| 5,922,014 A | 7/1999 | Warman et al. | |
| 5,938,694 A | 8/1999 | Jaraczewski et al. | |
| 6,006,134 A | 12/1999 | Hill et al. | |
| 6,132,384 A | 10/2000 | Christopherson et al. | |
| 6,212,435 B1 | 4/2001 | Lattner et al. | |
| 6,266,564 B1 | 7/2001 | Hill et al. | |
| 6,314,324 B1 | 11/2001 | Lattner et al. | |
| 6,360,740 B1 | 3/2002 | Ward et al. | |
| 6,415,183 B1 | 7/2002 | Scheiner et al. | |
| 6,449,507 B1 | 9/2002 | Hill et al. | |
| 6,463,327 B1 | 10/2002 | Lurie et al. | |
| 6,532,388 B1 | 3/2003 | Hill et al. | |
| 6,537,228 B1 | 3/2003 | Lambert | |
| 6,542,774 B2 | 4/2003 | Hill et al. | |
| 6,587,726 B2 | 7/2003 | Lurie et al. | |
| 6,641,542 B2 | 11/2003 | Cho et al. | |
| 6,684,101 B2 | 1/2004 | Daum | |
| 6,718,208 B2 | 4/2004 | Hill et al. | |
| RE38,705 E | 2/2005 | Hill et al. | |
| 6,881,192 B1 | 4/2005 | Park | |
| 6,890,306 B2 | 5/2005 | Poezevera | |
| 6,928,324 B2 | 8/2005 | Park et al. | |
| 6,934,583 B2 | 8/2005 | Weinberg et al. | |
| 6,937,903 B2 | 8/2005 | Schuler et al. | |
| 6,964,641 B2 | 11/2005 | Cho et al. | |
| 7,025,730 B2 | 4/2006 | Cho et al. | |
| 7,070,568 B1 | 7/2006 | Koh | |
| 7,077,132 B2 | 7/2006 | Berthon-Jones | |
| 7,082,331 B1 | 7/2006 | Park et al. | |
| 7,094,207 B1 | 8/2006 | Koh | |
| 7,155,278 B2 | 12/2006 | King et al. | |
| 7,179,229 B1 | 2/2007 | Koh | |
| 7,184,829 B2 | 2/2007 | Hill et al. | |
| 7,200,442 B1 | 4/2007 | Koh et al. | |
| 7,212,862 B2 | 5/2007 | Park et al. | |
| 7,223,244 B1 | 5/2007 | Koh | |
| 7,225,019 B2 | 5/2007 | Jahns et al. | |
| 7,225,021 B1 | 5/2007 | Park et al. | |
| 7,245,971 B2 | 7/2007 | Park et al. | |
| 7,269,457 B2 | 9/2007 | Shafer et al. | |
| 7,269,459 B1 | 9/2007 | Koh | |
| 7,277,757 B2 | 10/2007 | Casavant et al. | |
| 7,340,302 B1 | 3/2008 | Falkenberg et al. | |
| 7,357,775 B1 | 4/2008 | Koh | |
| 7,361,146 B1 | 4/2008 | Bharmi et al. | |
| 7,363,086 B1 | 4/2008 | Koh et al. | |
| 7,371,220 B1 | 5/2008 | Koh et al. | |
| 7,813,805 B1 | 10/2010 | Farazi | |
| 8,140,164 B2 * | 3/2012 | Tehrani | A61N 1/3601 607/42 |
| 8,233,987 B2 * | 7/2012 | Gelfand et al. | 607/42 |
| 2001/0003799 A1 | 6/2001 | Boveja | |
| 2002/0049479 A1 | 4/2002 | Pitts | |
| 2002/0128563 A1 | 9/2002 | Carlson et al. | |
| 2003/0078623 A1 | 4/2003 | Weinberg et al. | |
| 2003/0088244 A1 | 5/2003 | Swanson et al. | |
| 2003/0195571 A1 | 10/2003 | Burnes et al. | |
| 2005/0043765 A1 | 2/2005 | Williams et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0107838 A1 | 5/2005 | Lovett et al. | |
| 2005/0165457 A1 * | 7/2005 | Benser et al. | 607/42 |
| 2005/0197588 A1 | 9/2005 | Freeberg | |
| 2005/0240240 A1 | 10/2005 | Park et al. | |
| 2005/0288729 A1 | 12/2005 | Libbus et al. | |
| 2006/0030894 A1 | 2/2006 | Tehrani | |
| 2006/0036294 A1 | 2/2006 | Tehrani | |
| 2006/0084060 A1 | 4/2006 | Nagahama et al. | |
| 2006/0122662 A1 | 6/2006 | Tehrani et al. | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0229677 A1 | 10/2006 | Moffitt et al. | |
| 2006/0247729 A1 | 11/2006 | Tehrani et al. | |
| 2007/0021795 A1 | 1/2007 | Tehrani | |
| 2007/0118183 A1 | 5/2007 | Gelfand et al. | |
| 2007/0156199 A1 | 7/2007 | Koh et al. | |
| 2007/0260285 A1 | 11/2007 | Libbus et al. | |
| 2008/0154330 A1 | 6/2008 | Tehrani et al. | |
| 2008/0161878 A1 | 7/2008 | Tehrani et al. | |
| 2008/0167695 A1 | 7/2008 | Tehrani et al. | |
| 2008/0177347 A1 | 7/2008 | Tehrani et al. | |
| 2008/0183239 A1 * | 7/2008 | Tehrani et al. | 607/42 |
| 2008/0183240 A1 | 7/2008 | Tehrani et al. | |
| 2008/0183254 A1 | 7/2008 | Bly et al. | |
| 2008/0183259 A1 | 7/2008 | Bly et al. | |
| 2008/0183264 A1 | 7/2008 | Bly et al. | |
| 2008/0188903 A1 | 8/2008 | Tehrani et al. | |
| 2008/0188904 A1 | 8/2008 | Tehrani et al. | |
| 2008/0234694 A1 | 9/2008 | Stegfeldt et al. | |
| 2009/0062882 A1 * | 3/2009 | Zhang et al. | 607/42 |
| 2009/0088827 A1 | 4/2009 | Tockman et al. | |
| 2010/0249630 A1 | 9/2010 | Droitcour et al. | |
| 2011/0060380 A1 | 3/2011 | Gelfand et al. | |
| 2012/0158091 A1 * | 6/2012 | Tehrani et al. | 607/42 |

FOREIGN PATENT DOCUMENTS

| | | |
|---|---|---|
| WO | 2008/046190 A1 | 4/2008 |
| WO | 2008092246 A1 | 8/2008 |

OTHER PUBLICATIONS

Extended European Search Report dated Sep. 16, 2016 for corresponding European Patent Application No. 15192744.9, filed Nov. 3, 2015.

Chinese Office Action dated Nov. 28, 2016 for corresponding Chinese Application No. 201080040438.2.

Redline, Susan et al., Beyond the Fat Boy, Journal of Applied Physiology 2005, vol. 99: pp. 1243-1244.

Esler, Murray et al., Is Obstructive Sleep Apnea the Cause of Sympathetic Nervous Activation in Human Obesity?, Journal of Applied Physiology 2006, vol. 100, pp. 11-12.

Caples, Sean M. et al., Influence of Cardiac Function and Failure on Sleep-Disordered Breathing, Journal of Applied Physiology 2005, vol. 99, pp. 2433-2439.

Punjabi, Naresh M. et al., Hypoxia Augments Apnea-Induced Peripheral Vasoconstriction in Humans, Journal of Applied Physiology 2001, vol. 90, pp. 1516-1522.

Leuenberger, Urs et al., Hypoxia Augments Apnea-Induced Peripheral Vasoconstriction in Humans, Journal of Applied Physiology 2001, vol. 90, pp. 1516-1522.

Ishii, Kiyoshi, Effects of Bilateral transvenous diaphrahm pacing on hemodynamic function in patients after cardiac operations, 1990.

Parati, Gianfranco et al., Sleep Apnea: Epidemiology, Pathophysiology, and Relation to Cardiovascular Risk, Am Journal Physiological Society 2007, vol. 293, pp. R1671-R1683.

Gottfried, Stewart B. et al., Effects of Phrenic Stimulation on Upper Airway Resistance in Anesthetized Dogs, Am Physiological Society 1983, 0161-7567/83 pp. 419-426.

Planas, Roque F. et at, Diaphragmatic Pressures: Transvenous vs. Direct Phrenic Nerve Stimulation, Am Physiological Society 1985, 0161-07567/85, pp. 269-273.

Series, F. et al., Site of Phrenic Nerve Stimulation-Induced Upper Airway Collapse: Influence of Expiratory Time, Journal of Applied Physiology 2002, vol. 92, pp. 665-671.

Kingma, John G. Jr. et al., Nueromodulation Therapy Does Not Influence Blood Flow Distribution or Left-Ventricular Dynamics During Acute Myocardial Ischemia, Autonomic Neuroscience; Basic and Clinical 91 (2001) pp. 47-54.

(56) References Cited

OTHER PUBLICATIONS

Linderoth, Bengt, MD, PhD et al., Mechanisms of Spinal Cord Stimulation in Painful Syndromes: Role of Animals Models, American Academy of Pain Medicine, vol. 7, No. S14-S26, 2006.
Tanaka, Satoshi et al., Mechanisms of Sustained Cutaneous Vasodilation Induced by Spinal Cord Stimulation, Autonomic Neuroscience: Basic and Clinical 114 (2004) pp. 55-60.
Lorenzi-Filho, Geraldo et al., Cheye-Stokes Respiration in Patients with Congestive Heart Failure: Causes and Consequences, Clinics 2005; 60 (4): 333-44.
Brack, Thomas, Cheye-Stokes Respiration in Patients with Congestive Heart Failure, Seiss Med Wkly 2003; 133:605-610, www.smw.ch.
Yumino, Dai et al., Central Sleep Apnea and Cheyne-Stokes Respiration, Proceedings of the American Thoracic Society, 2008, vol. 5, pp. 226-236.
Garrido-Garcia, H. et al., Treatment of Chronic Ventilatory Failure Using a Diaphragmatic Pacemaker, Spinal Cord (1998) 36, 310-314.
Diedrichs, Holger et al., Symptomatic Relief Precedes Improvement of Myocardial Blood Flow in Patients Under Spinal Cord Stimulation, BioMed Central, 2005, pp. 1-7.
Kaneko, S. et al., A New Approach to Respiratory ASsist for Phrenic Nerve Paralysis, Trans Am Soc. Artif Intern Organs, 1985, vol. XXI, pp. 301-304.
Kohnlein, T. et al., Central Sleep Apnea Syndrome in Patients with Chronic Heart Disease: A Critical Review of the Current Literature, Thoarx 2002; 57:547-554.
Javaheri, Shahrokh, MD, Central Sleep Apnea in Congestive Heart Failure: Prevalence, Mechanisms, Impact, and Therapeutic Options, Seminars in Respiratory and Critical Care Medicine, 2005, vol. 26, No. 1.
Dobelle, Wiliam H., Use of Breathing Pacemakers to Suppress Intractable Hiccups of up to Thirteen Years Duration, ASAIO Journal 1999, pp. 524-525.
Series, Frederic, Assessment of Upper Airway Dynamics in Awake Patients with Sleep Apnea Using Phrenic Nerve Stimulation, Am Journal Respir Crit Care Med, 2000, vol. 162., pp. 795-800.
Bilgutay, A.M. et al, Augmented Ventilation by Synchronous Phrenic Nerve Stimulation, Trans. Amer. Soc. Artif. Int. Organs, 1970, vol. XVI, pp. 213-217.
Yasuma, Fumihiko et al., Eight-Year Follow-Up Study of a Patient with Central Alveolar Hypoventilation Treated with Diaphragm Pacing, Respiration, 1998: 65:313-316.
Handa, Y. et al., Basic Studies on Electrophrenic Respiration Pat 2-Assisted Ventilation by the Synchronous Electrophrenic Respirator, Medical and Biological Engineering, Jul. 1976.
Kimura, M. et al., A Heart-Rate-Responsive Diaphragm Pacemaker, Med. & Biol. Eng. & Comput., 1987, 25, 458-462.
Kimura, M. et al., Heart Rate and Body Temperature Sensitive Diaphragm Pacing, Med. & Biol. Eng. & Comput. 1992, 30, 155-161.
Kimura, M. et al., Addition to an RF-Coupled Phrenic Nerve Stimulator Implant to Provide Outward Transmission of Body Temperature, Med. & Biol. Eng. & Comput. 1986, 245, 659-661.
Taira, Takaomi, MD, Ph. D. et al., Phrenic Nerve Stimulation for Diaphragm Pacing with a Spinal Cord Stimulator, Elsevier Science, Surg Neurol, 2003; 59:128-32.
Sarnoff, Stanley J. et al., Electrophrenic Respiration. III. Mechanism of the Inhibition of Spontaneous Respiration, Dept. of Physiology, Harvard School of Public Health, 1948, vol. 155, pp. 203-207.
Sarnoff, Stanley J. et al., Electrophrenic Respiration IV. The Effectiveness of Contralateral Ventilation During Activity of One Phrenic Nerve, Dept. of Physiology, Harvard School of Public Health, 1949, pp. 929-937.
Stemmer, Edward A. MD et al., Diaphragmatic Pacing in the Treatment of Hypoventilation Syndrome, Journal of Thoracic and Cardiovascular Surgery, vol. 54, No. 5, 1967, pp. 649-657.
Furman, Seymour MD et al., Transvenous Stimulation of the Phrenic Nerves, Journal of Thoracic and Cardiovascular Surgery, vol. 62, No. 5, 1971, pp. 743-751.
Aiyar, Harish et al., Diaphragm Pacing for Chronic Respiratory Insufficiency, CRC Press, LLC, 2001, Chapter 9.
Oliven, Arie et al., Upper Airway Response to Electrical Stimulation of the Geniglossus in Obstructive Sleep Apnea, Journal of Applied Physiology, 95:2023-2029, 2003.
International Search Report dated for Oct. 29, 2010 for International Application No. PCT/US2010/045992.
Written Opinion dated for Oct. 29, 2010 for International Application No. PCT/US2010/045992.
Javaheri, Shahrokh, Md, Acetazolamide Improves Central Sleep Apnea in Heart Failure Pulmonary Service, Department of Veterans Affairs Medical Center, and Department of Medicine, University of Cincinnati College of Medicine, Cincinnati, Ohio Am J Respir Crit Care Med vol. 173. pp. 234-237, 2006, Jul. 5, 2005.
Vaseghi, et al., Beyond Coronary Sinus Angiography: The Value of Coronary Arteriography and Identification of the Pericardiophrenic Vein During Left Ventricular Lead Placement, PACE, 2005, vol. 28.
Leung, Richard S. T. et al., Influence of Cheyne-Stokes Respiration on Cardiovascular Oscillations in Heart Failure, Am J Respir Crit Care Med, 2003, vol. 167. pp. 1534-1539.
Escher, Doris J.W., Clinical control of Respiration by Transvenous Phrenic Pacing, Trans. Amer. Soc. Artif. Int. Organs., vol. XIV, 1968.
Levy, T. et al., A Comparison Between Passive and Active Fixation Leads in the Coronary Sinus for Biatrial Pacing, The European Society of Cardiology 2000.
Javaheri, Shahrokh M.D., CPAP Should Not Be Used for Central Sleep Apnea in Congestive Heart Failure Patients, Journal of Clinical Sleep Medicine, vol. 2, No. 4, 2006.
Hall, Michael J. et al., Cycle Length of Periodic Breathing in Patients with and without Heart Failure, Am. J. Respir. Crit. Care Med vol. 154. pp. 379-381, 1996.
Hasdemir, Can MD et al., Jpn Heart J., vol. 44 No. 3, 2003.
Schauerte, Patrick et al., Catheter Stimulation of Cardiac Parasympathetic Nerves in Humans: A Novel Approach to the Cardiac Autonomic Nervous System, American Heart Association 2006.
Shaul, Donald B., et al., Thoracoscopic Placement of Phrenic Nerve Electrodes for Diaphragmatic Pacing in Children, Journal of Pediatric Surgery, vol. 37, No. 7 pp. 974-978, 2002.
Plisiene, Jurgita et al., Selective Transvascular Stimulations of Cardiac Autonomic Nerves: A Novel Technique, Biomedicine vol. 2 No. 1, Jul. 2002.
Arzt, Michael et al., Treatment of Sleep Apnea in Heart Failure, Am J Respir Crit Care Med vol. 173. pp. 1300-1308, 2006.
Thoma, H. et al., The Vienna Phrenic Pacemaker, Longterm Data of Failures.
International Search Report dated Aug. 19, 2010 for International Application No. PCT/US2010/045992.
Restriction Requirement from United States Patent and Trademark Office dated Mar. 23, 2009 for U.S. Appl. No. 11/601,150.
Office Action from United States Patent and Trademark Office dated Aug. 20, 2009 for U.S. Appl. No. 11/601,150.
Final Office Action from United States Patent and Trademark Office dated Jun. 8, 2010 for U.S. Appl. No. 11/601,150.
European Office Action dated Sep. 30, 2010 for European Application No. 06 837 985.8-2305.
European Search Report dated Aug. 12, 2009 for European Application No. 06837985.
European Search Report dated Aug. 19, 2011 for European Application No. 11170415.
International Search Report and Written Opinion dated Aug. 15, 2007 for International Application No. PCT/US06/44788.
Chinese Office Action dated Dec. 19, 2017 for corresponding Chinese Application No. 201610245292.4, filed Apr. 19, 2016.

* cited by examiner

RESPIRATORY RECTIFICATION

CROSS REFERENCE TO RELATED APPLICATIONS

This application is a Continuation of U.S. patent application Ser. No. 12/557,084, now U.S. Pat. No. 8,233,987 filed Sep. 10, 2009, titled "Respiratory Rectification."

SUMMARY

In humans, gas exchange is accomplished by rhythmic inflation and deflation of lungs. During ventilatory movements, the lung is passive and its volume is determined by the size of the thorax, which in turn is dependent mainly on the activity of the intercostal muscles and the diaphragm.

Vertical movement of diaphragm is about 1.5 cm during quiet breathing and may go up to 7 cm in deep breathing. A descent of the diaphragm by 1 cm will increase the thoracic capacity by approximately 300 mL and cause a corresponding volume of air to enter the lungs. Thus, the movements of the diaphragm may be responsible for about 60-80% of lung distention and the total air breathed.

A respiratory control center in the brain controls respiratory muscles. Respiratory muscles consist of the respiratory pump (diaphragm and intercostal muscles) and airway muscles. Neural signals that travel to the respiratory muscles constitute the central respiratory drive. While the diaphragm is the main source of power for the respiratory pump, the function of airway muscles is to keep the airway open. Without central neural drive the airway may collapse or partially occlude.

During sleep the respiratory control is unconscious and governed by metabolic demand (mainly the need to remove CO2 from blood). In all humans, the central neural drive to the respiratory pump and airway muscles during sleep is reduced compared to an awake state. In the presence of a mild pathology, airway resistance to airflow can be increased during sleep resulting in, for example, snoring. In extreme cases the airway can close completely resulting in obstructive sleep apnea (OSA). In some cases deregulation of the central control can result in periodic breathing and severe disease that can damage multiple organs.

Central Sleep Apnea (CSA) is a form of periodic breathing characterized by an oscillating central respiratory drive. CSA may be characterized by a typical waxing and waning respiratory pattern made up of alternating apneas and hyperpneas (periods of hyperventilation), historically called Cheyne Stokes Respiration (CSR).

Obstructive Sleep Apnea (OSA) is characterized by upper airway instability. A collapsed airway prevents or reduces inspiration in the face of continuing or increasing respiratory effort. A common pattern of OSA in the general population is characterized by periodic arousals that result in abrupt opening of the airway.

Inventors have discovered that in some patient populations, such as those with congestive heart failure (CHF) for example, it is difficult if not impossible to separate the underlying mechanisms of OSA and CSA. A purely central CSR pattern is somewhat rare. Common presentation of periodic breathing in CHF patients may consist of alternating respiratory events that can include hyperpneas, hypopneas, and central, obstructive and mixed apneas. A significant overlap exists, and most patients experience varying degrees of both central and obstructive events. Indeed, it is believed that oscillating central respiratory drive may lead to upper airway closure or increased resistance.

Following an extensive series of experiments, inventors realized that effective treatment of many cases of periodic breathing required addressing central neural drive to breathe as well as airway issues. Because of the relationship between respiratory pump muscles and airway muscles, inventors desired to modulate the brain's intrinsic respiratory activity to affect both aspects of respiration. The brain's respiratory control center is located in the medulla of the brain and is not directly accessible for modern neuromodulation technologies. The inventors were therefore compelled to investigate neural inputs to the brain that govern the behavior of the respiratory control center.

The brain's respiratory control center receives inputs from chemoreceptors in the arterial vasculature (in the aortic arch, carotid bodies and blood vessels in the brain itself) and from mechanoreceptors such as the respiratory pump muscles, pulmonary stretch receptors in the lung, and intercostal stretch receptors. It is known that altering input into the brain from chemoreceptors by making the patient breathe in some carbon dioxide can control periodic breathing.

Phrenic nerves control the motion of the diaphragm, which in turn can lead to activation of series of neural inputs to the brain, for example by stretching various innervated tissues in the thorax. The Hering-Breuer reflex is a powerful neural feedback from the lung stretch receptors to the brain. When the lung is inflated and stretched, the respiratory center of the brain suspends the respiratory drive. It is believed that entrainment of respiration to external stimulus in sleeping humans involves the Hering-Breuer reflex as well as other neural inputs.

The technology inventors chose for investigation was phrenic nerve stimulation. One form of phrenic nerve stimulation known as "electrophrenic ventilation" or "diaphragmic pacing" has been used for many years to replace intrinsic breathing. The physiology of respiratory pacing is straightforward. The phrenic nerve is stimulated to take over respiration by slightly hyperventilating the patient. The consequent reduction of blood carbon dioxide concentration is sensed by the brain's respiratory control center and substantially all the neural output from the center (central respiratory drive) stops. A patient, thus paced, may not experience respiratory disturbances while paced but becomes temporarily dependant on phrenic "pacing" for ventilation and gas exchange.

Such phrenic pacing was used to treat Paraplegics and Central Congenital Hypoventilation Syndrome in children since the 1960s and successfully prevented death by replacing natural respiration drive with artificial one. By taking over breathing, such pacing suppresses intrinsic central respiratory drive. While eliminating oscillations of respiratory drive it also may eliminate the drive to keep the airway open. In patients with Central Congenital Hypoventilation Syndrome this limitation can be overcome by tracheostomy (a surgical procedure on the neck to open a direct airway through an incision in the trachea). A tracheostomy is unacceptable in patients with periodic breathing.

By contrast, embodiments in accordance with the invention apply stimulation to only one phrenic nerve at a constant rate that is in some embodiments slightly below the patient's intrinsic rate. These embodiments may result in the entrainment of the patient's central respiratory activity rather than suppression of the intrinsic drive. When applied during periodic breathing in sleeping individuals, and delivered within a particular range of stimulation parameters, this form of phrenic nerve stimulation often resulted in die restoration of normal breathing rhythm, was sustainable, and was well tolerated during natural sleep.

In some embodiments in accordance with the invention, stimulation results in rhythmic contractions of one hemidiaphragm innervated by the stimulated nerve and consequent rhythmic lung inflations. The patient's intrinsic breathing rhythm is modulated by stimulation, becoming more regular and exhibiting less periodicity. The improvement in breathing is believed to be achieved by the mechanism of lung distension and entrainment of the neurons in the brain respiratory center, among other mechanisms, rather than by control of breathing per se. Spontaneous breathing and central respiratory drive are preferably preserved, thus resulting in the benefit of maintained airway muscle tone and natural blood gas regulation.

Another embodiment in accordance with the invention concerns monitoring and controlling diaphragmatic stimulation and entrainment of stimulation. This embodiment is based on the assumption that when stimulation entrains respiration, the spectral power of the respiratory signal in the immediate range of the driving frequency will be significantly higher than in other frequency bands. In one embodiment a ratio of total variance of respiration signal that falls into the narrow band centered on the stimulation frequency to the total variance in the broader respiratory frequency band can be calculated. It can be expected that the value of this ratio will increase proportionally to the entrainment of respiration by stimulation, thus enabling guided and calibrated therapy based on the effect of stimulation on actual respiration. Two exemplary calculation methods are disclosed herein for such a ratio: the spectrum method and the histogram method. It is to be understood that these methods are not the only ways to determine entrainment or nerve or muscle capture efficacy by frequency analysis, and other methods will occur to those of skill in the art upon reading this disclosure.

Inventors observe occasional regularization of breathing rhythm and resolution of both central and obstructive apnea during unilateral phrenic stimulation. Inventors saw that the phrenic stimulation prevents and corrects the intrinsic periodicity of breathing in patients that frequently exhibit oscillatory respiration during sleep. Inventors observe that the patient's breathing, previously highly irregular, gradually becomes tuned to the rhythm of phrenic stimulation and follows it if the rate of stimulation was changed. Inventors have also observed fixed and repetitive coupling between the external stimulus and neural inspiratory activity in the respiratory control center of the brain. Inventors confirmed that the patient breathing was entrained, and indeed spontaneous, by making the following observations:

(1) When stimulation was abruptly stopped the patient did not stop breathing. In some cases patients continued breathing "as if still stimulated" following the no-longer-present cues for several minutes before reverting back to the pre-stimulation pattern.

(2) Because only one phrenic nerve was stimulated, the second lung was free to inflate and deflate without the direct influence of stimulation. Inventors confirmed the independent motion of the un-stimulated lung by separate transthoracic impedance measurements.

(3) Frequently, patients were observed to insert or interlace spontaneous small breaths in between breaths entrained to the stimulation, thus confirming that the central respiratory drive remained active. These interlaced breaths did not interfere with the pattern of entraining.

It is believed that stabilization of blood gases and the elimination or reduction of intermittent hypoxia and arousals associated with hyperventilation through entrainment with phrenic stimulation improves airway tone. Hypoxia in an exceptionally strong stimulus to hyperventilate, as is the neurologic arousal that often follows hypoxia. The severity of hyperventilation that follows the intermittent hypoxia determines the subsequent reduction of blood $CO_2$ that results in the withdrawal of the neural stimulus to both respiratory pump muscles and the airway muscles. The inverse is also true. The reduction of hypoxia and the subsequent hypoxia-exacerbated hyperventilation should help sustain respiratory drive and maintain neural muscle tone of the airway after the transient hyperpnea is over.

Another way in which the CSA is thought to reduce upper airway stability and induce OSA is by promoting periods of hypopnea. During hypopnea, the activity of both respiratory pump muscles (e.g. diaphragm) and upper airway dilator muscles (e.g. genioglossus) is reduced. Therefore, a waxing-waning pattern of central respiratory drive in an individual having an upper airway prone to collapse may result in to obstructive apnea/hypopnea during the periods of hypopnea because of upper airway hypotonia (low muscle tone). It is reasonable to assume that the opposite is also true. Reducing hypopnea in CSA patients will help stabilize the airway by increasing airway muscle tone.

In the context of this disclosure, hypopnea broadly refers to a transient reduction of airflow (while asleep) that lasts for at least 10 seconds because of transient shallow breathing, or an abnormally low respiratory rate. In medical literature breathing that is too shallow (hypopnea) or too slow (bradypnea) is sometimes differentiated. Hypopnea is less severe than apnea (which is a more complete loss of airflow) but can likewise result in a decreased amount of air movement into the lungs and can cause oxygen levels in the blood to drop (hypoventilation).

There is no firm scientific consensus on the narrow or quantitative definition of hypopnea and it is understood that many definitions are often used in scientific literature and can be applied.

For example in their research, which served as a basis for this disclosure, inventors used transient reduction of respiration (airflow) by >30% for the duration of 10 to 60 seconds accompanied by detectable (4%) oxygen desaturation as the quantitative "technical" definition of hypopnea. Within the narrow scope of this quantitative definition, hypopnea and transient hypoventilation are for all practical purpose equivalents.

When defined broadly hypoventilation is the state in which a reduced amount of air enters the alveoli in the lungs, resulting in decreased levels of oxygen and/or increased levels of carbon dioxide in the blood. Hypoventilation can also be defined broadly, and perhaps better, as breathing that is not adequate to meet the needs of the body. Hypoventilation can be due to hypopnea or to diminished lung function. Hypoventilation can be transient (as a result of hypopnea) or sustained due to various pathologies such as in congenital disease, Chronic Obstructive Pulmonary Disease (COPD) or obesity.

Periodic lung inflations play an important role in the maintenance of neural sympathetic-parasympathetic balance, heart rhythm and blood pressure regulation. As early as in the 1940s many of these physiologic interactions were traced to neural feedbacks that signal lung expansion to the autonomic nervous system. The role of the autonomic nervous system in the body's homeostasis is particularly important during sleep. These beneficial feedbacks have been graded according to lung inflation.

The importance of neural feedbacks from the stretch receptors in the lungs to the multiple brain centers that control cardiovascular activity may be best demonstrated by so called Respiratory sinus arrhythmia. Respiratory sinus arrhythmia (RSA) is a heart rate change that occurs in synchrony with respiration, by which the R-R interval on an ECG is shortened during inspiration and prolonged during expiration. Although RSA has been used as an index of cardiac vagal function, it is also a physiologic phenomenon reflecting respiratory-circulatory interactions universally observed among vertebrates. Studies have shown that the efficiency of pulmonary gas exchange is improved by RSA, suggesting that RSA may play an active physiologic role. The matched timing of alveolar ventilation and its perfusion with RSA within each respiratory cycle could reduce energy expenditure by suppressing unnecessary heartbeats during expiration and ineffective ventilation during the ebb of perfusion. RSA or heart rate variability in synchrony with respiration is a biological phenomenon, which may have a positive influence on gas exchange at the level of the lung via efficient ventilation/perfusion matching.

Inventors observed increase of RSA when patients with CHF were treated in accordance with embodiments of the invention. It is reasonable to expect that other benefits such as dilation of blood vessels and reduction of malignant arrhythmias will follow.

Phrenic or diaphragm stimulation in accordance with embodiments of the invention can expand the breath or lung volume to combat the effects of hypopnea. Stimulation is also expected to result in sustained lung expansions as opposed to the waxing and waning pattern found in CSA. Additional airway tone benefit can be expected from these improvements. In patients with significant CSA, upper airway collapse and resulting OSA may be secondary to the withdrawal of neural and mechanical stimulus to the airway caused by reduced parasympathetic activation and diminished lung inflation during central apnea/hypopnea episodes.

Clinical benefit can be derived from the entrainment of the intrinsic respiratory rhythm by stimulation. Increased lung volume, stabilized blood gas composition and reduced hypoventilation all suggest improvement of airway dynamics in addition to the primary correction of central respiratory instability.

Upper airway dilator muscles play an important role in maintaining airway patency. Many of the pharyngeal dilator muscles are known to demonstrate inspiratory phasic activity, the onset of which precedes diaphragmatic activity. That is, the airway muscles contract in phase with respiration slightly prior to the respiratory pump muscles, thus "preparing" the pharyngeal airway for the development of negative pressure during inspiration.

The best studied pharyngeal muscle is the genioglossus. The genioglossus receives input from the brain respiratory control center (or more precisely from the brainstem respiratory central pattern generator) located in the medulla. The hypoglossal nerve activates the genioglossus, and the hypoglossal nerve has been detected firing 50-100 ms prior to the phrenic nerve in healthy patients.

Chemoreceptive inputs are also important in influencing hypoglossal motor nerve output. Low blood CO2 (hypocapnea) reduces activation and high CO2 (hypercapnea) increases it. Thus it may be useful for any periodic breathing treatment to avoid hypocapnea and the reduced airway muscle activation that accompanies hypocapnea.

Embodiments in accordance with the invention are usable to treat periodic breathing in sleeping patients, but they can also be used to regularize breathing in resting people with ischemic heart disease, heart allure, hypertension, COPD, and other conditions where improved breathing efficacy is advantageous.

In one embodiment in accordance with the invention, a measured frequency zone is defined based on measured physiological signals associated with the intrinsic contraction of a muscle. A stimulation frequency zone is defined based on stimulation frequency of an electrical pulse generator configured. to stimulate the muscle or a nerve associated with the muscle at a different frequency than the intrinsic frequency. The muscle or a nerve associated with the muscle is stimulated, and the impact of stimulation is determined by comparing the measured power of an array of signals that fall within the measured frequency zone to the measured power of the array of signals that fall within the stimulation frequency zone. In variations of this embodiment, the physiological signal is a signal representative of respiration. In another embodiment, the muscle is a diaphragm muscle. In yet another embodiment, the measured frequency zone comprises a range of frequencies proximate the respiration frequency of a patient.

In another embodiment in accordance with the invention, a system for electrical stimulation of a nerve or muscle includes an electrical pulse generator that delivers energy to stimulate a muscle at a first frequency, the first frequency different from a second frequency at which the muscle intrinsically contracts. The system of this embodiment also has a sensor that senses physiologic activity indicative of contraction of the stimulated muscle and an electronic memory to store an array of data generated by the sensor over a period of time. A frequency analyzer analyzes the array of data to determine the power distribution across a frequency band for the sensed physiologic activity and circuitry of the system is capable of comparing the power in a band proximate the stimulation frequency to the total power across the frequency band for the sensed physiologic activity.

In another embodiment in accordance with the invention, a system for electrical stimulation of a nerve or muscle includes an electrical pulse generator that delivers energy to stimulate a muscle at a first frequency, the first frequency different from a second frequency at which the muscle intrinsically contracts. The system of this embodiment also has a sensor that senses physiologic activity indicative of contraction of the stimulated muscle and an electronic memory to store an array of data generated by the sensor over a period of time. A frequency analyzer analyzes the array of data to determine the power distribution across a frequency band for the sensed physiologic activity and circuitry of the system is capable of comparing the power in a band proximate the stimulation frequency to the total power across the frequency band for the sensed physiologic activity. In this embodiment, the circuitry is capable of increasing the energy delivered by the pulse generator if the ratio of the power in the band proximate the stimulation frequency to the total power is below a threshold.

In another embodiment in accordance with the invention, a system for treating disordered breathing includes an electrical pulse generator capable of providing electrical stimulation signals to a phrenic nerve or diaphragm of a patient at a predetermined signal frequency. This embodiment has a respiration sensor capable of sensing a signal representative of the patient's respiration and a frequency comparator that compares the power density of the frequency distribution of sensed respiration signals over a stimulation frequency band to the power density of sensed respiration signals over a respiratory frequency band The system includes power adjusting circuitry that adjusts the power of the electrical stimulation signals provided by the electrical pulse generation based on the comparison of the power densities. In various embodiments, the power adjusting, circuitry could adjust stimulation current, stimulation voltage, The frequency of the pulses in a pulse train, a pulse duration of the pulses in a pulse train, or other parameters.

In yet another embodiment in accordance with the invention, a phrenic nerve or diaphragm is stimulated at a frequency below an intrinsic breathing rate. The stimulation is delivered at an intensity sufficient to entrain respiration while leaving intrinsic drive to breathe intact. In some embodiments, respiratory drive is manifested as 2:1 entrainment, in others as spontaneous breathing of an unstimulated lung, in others as minor breaths interlaced among entrained breaths, and in others as periodic activation of airway muscles.

In another embodiment in accordance with the invention, disordered breathing is treated by detecting a signal representative of the respiration of a patient and conducting a frequency analysis of the signal representative of respiration over a range of frequencies consistent with respiration. This embodiment includes the steps of determining an intrinsic breathing rate or frequency and stimulating one hemidiaphragm of the patient at a frequency different from the intrinsic breathing frequency. In this embodiment a frequency analysis of the respiration signal during stimulation is conducted. A capture index is determined by dividing the power distribution in a frequency range proximate the stimulation frequency to the power of the range of frequencies consistent with respiration to determine a capture index. Stimulation parameters are modified based on the calculated capture index. In some embodiments, the signal representative of respiration may be transthoracic impedance. In some embodiments, the stimulation frequency is lower than the intrinsic breathing frequency.

in another embodiment in accordance with the invention, disordered breathing is treated by detecting a signal representative of the respiration of a patient and conducting a frequency analysis of the signal representative of respiration over a range of frequencies consistent with respiration. This embodiment includes the steps of determining an intrinsic breathing rate or frequency and stimulating one hemidiaphragm of the patient at a frequency different from the intrinsic breathing frequency. In this embodiment a frequency analysis of the respiration signal during stimulation is conducted. A capture index is determined by dividing the power distribution in a frequency range proximate the stimulation frequency to the power of the range of frequencies consistent with respiration to determine a capture index. Stimulation parameters are modified based on the calculated capture index. In some embodiments the stimulation power is increased if the capture index is below a certain threshold. In some embodiments the stimulation power is decreased if the capture index is above a certain threshold.

DETAILED DESCRIPTION

Figure 1:
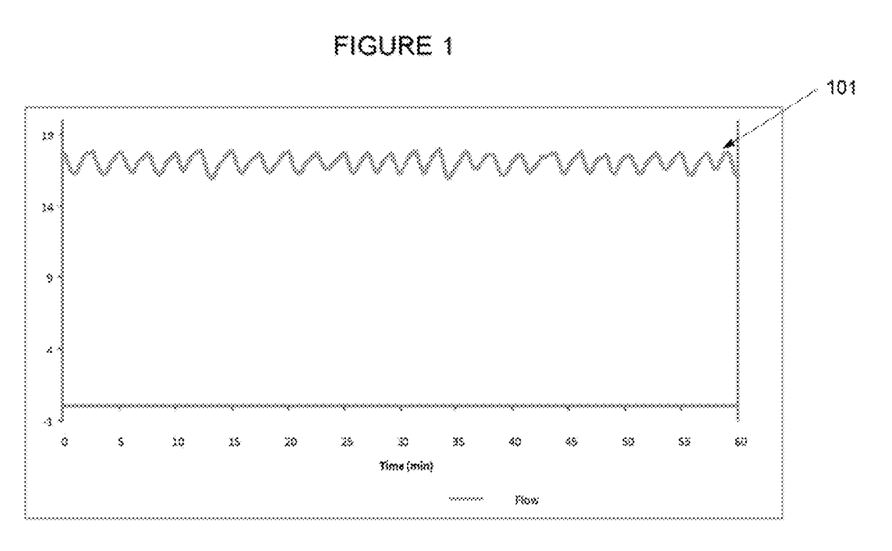
FIG. 1 is a waveform of the respiration data of an untreated patient.

FIG. 1 is a waveform of the respiration data of an untreated patient. The waveform represents 60 seconds of data acquired during the time when the patient was asleep. Trace 101 represents normal breathing (at rest) for this patient. The trace 101 was acquired at 10:42 pm just before the patient received therapy. The trace 101 represents airflow in and out of the patient lungs monitored with a flow meter (thermal sensor). At this time patient does not show periodic breathing or apneas and the patient is breathing regularly at 24 breaths per minute (0.4 Hz).

Figure 2:
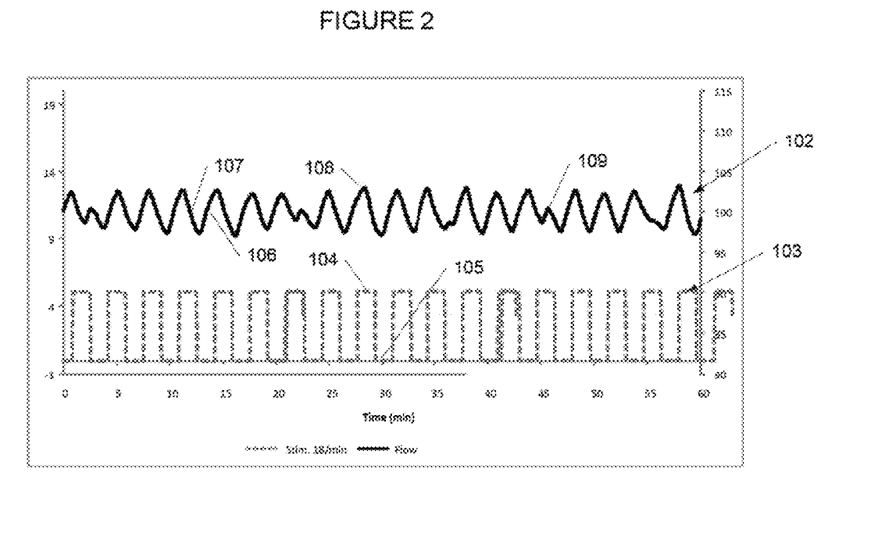
FIG. 2 is a waveform of the respiration of the patient of FIG. 1 during therapy in accordance with embodiments of the invention.

FIG. 2 is a waveform of the respiration of the patient of FIG. 1 during therapy in accordance with embodiments of the invention. This waveform also represents 60 seconds of data acquired when the patient was asleep. The patient has CSA and was treated using transvenous stimulation of the right phrenic nerve. Trace 103 represents stimulation pulse trains. The stimulation pulse trains were applied at a constant rate of 18 per minute (0.3 Hz puke rate), in this case below the patient's native breathing rate of 24 breaths per minute. Each pulse train is 1. 67 seconds long. During the pulse train application, the right phrenic nerve was stimulated and the right hemi-diaphragm muscles contracted (stimulation phase 104). Each pulse train is followed by the relaxation phase 105 that is also 1.67 seconds long in this example. During the relaxation phase the phrenic nerve is not stimulated. The stimulation pattern 103 represents therefore 50% duty cycle stimulation (50% inspiration-50% expiration). Other duty cycles or ratios can be used to achieve the objectives of the invention.

Each puke train 104 is composed of series of individual pukes (not shown) supplied by a pulse generator. The pulse generator can be external or implanted. In this example the pulses are 150 μs (microseconds) long and are applied at a 20 Hz frequency. The pulse generator of this example applied pulses in a controlled pre-programmed fashion to reach a pre-programmed peak current amplitude of 4.9 mA. To increase patient's comfort, the electric current amplitude of pulses within the pulse train may be gradually increased, held constant and then gradually decreased within the same pulse train. Other pulse train shapes may be used to elicit desired contraction and relaxation responses of the diaphragm muscle without deviating from the scope of this disclosure.

Trace 102 represents the respiration of the patient during the stimulation therapy. Similar to trace 101 from FIG. 1, it consists of individual breaths monitored by a flow meter. Each breath consists of an inspiration phase 106 and expiration phase 107. It can be noted that there are mostly large breaths 108 and some smaller breaths 109. Large breaths are phase locked with stimulation pulses 103 and the patient's breathing can be said to be entrained to the stimulation. These large breaths appear at the same rate as the stimulation pulse train rate of 18 per min (0.3 Hz).

When only large breaths appear in series they indicate the 1:1 entrainment (one breath for each stimulation pulse train). When small breaths appear, they may appear in a number of forms. In some cases, small breaths are interlaced between the large breaths at a rate that corresponds generally to the spontaneous breathing rate of 24 breaths per minute (0.4 Hz). In some cases, small breaths appear only occasionally as metabolic demand requires. In other cases, periods of interlaced breaths correspond to 2:1 entrainment (two breaths for each stimulation pulse train). In all cases the existence of small spontaneous or 2:1 entrained breaths support the inference that white breathing is entrained in this fashion the respiratory control center is still active While breaths on the trace 102 appear at the same basic frequency as the stimulation 103, they are not necessarily exactly synchronized to stimulation. Inspiration 106 can start at a different delay time following the start of stimulation pulse trains 104 and even can under certain circumstances precede the onset of the corresponding stimulation pulse train.

In the embodiment represented in FIG. 2, stimulation is applied at the rate somewhat lower than the spontaneous breathing rate at rest (in this example: 18 vs. 24/min). Stimulation may entrain spontaneous breathing but does not replace it. Entrainment is evidenced by the variable time delay and phase angle between the stimulation pulse trains and patients inspiration effort. Additional evidence of entrainment is the periodic appearance of 2:1 and 1:1 entrainment or other small breaths that are not entrained, which shows that respiratory drive is not suppressed, but entrained.

Figure 3:
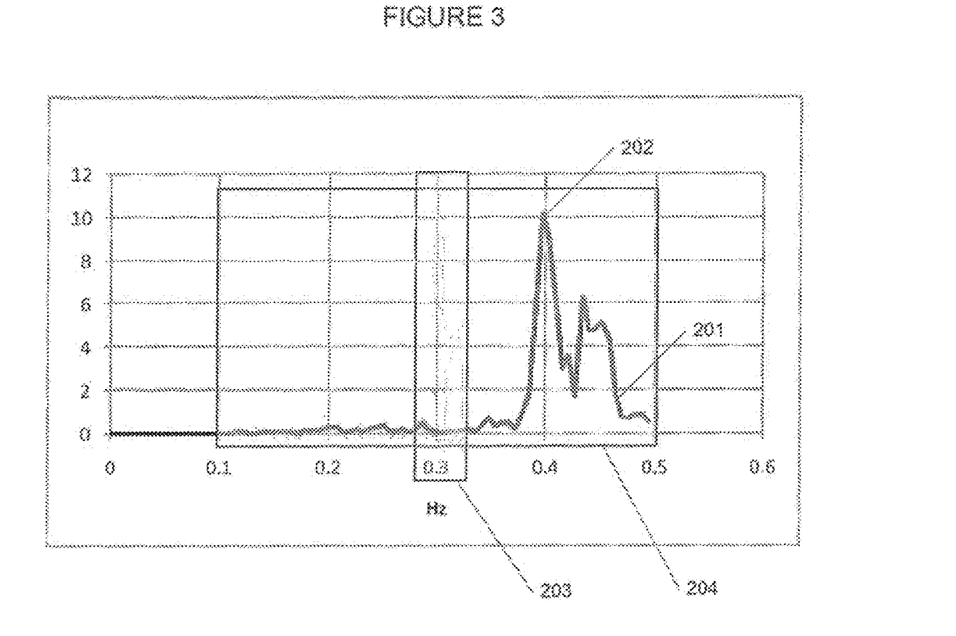
FIG. 3 is a spectral graph of the respiration data presented in FIG. 1.

FIG. 3 is a spectral graph of the respiration data presented in FIG. 1. Periodic waveforms such as breathing waveforms illustrated by FIG. 1 can be analyzed using various frequency domain methods, the most common of which is spectral analysis.

FIG. 3 shows spectrum of normal spontaneous breathing of the patient illustrated by the trace 101 on FIG. 1. Such spectrum can be obtained by performing Fast Fourier Transform (FFT) on 2-3 minutes of digitally acquired respiratory signal data (in this example, airflow). The spectrum can be a power spectrum, a power density spectrum or a magnitude spectrum. One can also think of the power spectrum as yielding which frequencies contribute most to the variance of the signal. The larger the amplitude, the higher the variance. This is a meaningful broad definition of "power spectrum." It is understood that many numerical methods exist for calculating frequency distribution of periodic signals, and all are contemplated herein. The "spectrum" may be calculated for the range of natural respiratory frequencies that generally are between 0 and 1.0 Hz. in the disclosed embodiment, the frequency range of approximately 0.1 to 0.5 Hz was found. The selected range is designated "respiratory frequency band" (RFB) for the purpose of this disclosure. Other frequency ranges could be selected and the selection of this range is merely exemplary.

In FIG. 3 the RFB 204 is indicated by the square frame that includes all respiratory frequencies important for the purpose of determining entrainment effectiveness in this example. The fact that the patient's natural respiration frequency peaks at 0.4 Hz 202 can be expected from the respiration trace 101 on FIG. 1. Another frequency band important for the determination of entrainment is designated "stimulation frequency hand" (SFB). It is represented by the narrow band square 203 and in this case is centered on the frequency at which stimulation pulse trains are applied as on trace 103 of FIG. 2.

The spectral graph of FIG. 3 corresponds to the period when stimulation therapy is not applied. Power in the SFB band is low if the central frequency, in this case 0.3 Hz, is significantly different from the dominant respiratory frequency 202.

The effectiveness of respiratory entrainment can be determined by comparing the spectral power in the SFB band to the total spectral power or to the spectral power in other frequency bands, for example. Inventors have found it useful to designate a Capture Index (CI) as a measure of therapy effectiveness. The capture index is calculated by dividing the spectral power in the SFB by the spectral power in the RFB. The capture index represents the fraction of total spectral plot of respiration that falls into the narrow band proximate the stimulation frequency. It can be expected that the value of capture index will increase proportionally with the entrainment of respiration by stimulation. The stimulation frequency thus becomes the dominant frequency of the respiration signal as entrainment increases. There are many numeric calculations that can be used to calculate capture index. For example, inventors used the following methodology, among others.

A spectral plot is a graphical technique for examining cyclic structure in the frequency domain. Strictly defined it is a smoothed Fourier transform of the autocovariance function. The frequency is measured in cycles per unit time. The spectral plot is displayed with a vertical axis of smoothed variance (power) and a horizontal axis of frequency (cycles per observation).

The computations for generating the smoothed variances can be involved and are not discussed further here. Spectral plots are a fundamental technique in the frequency analysis of time series and are familiar to those of skill in the art. Spectral plots may be used to determine how many cyclic components there are in a cyclic waveform, whether or not there is there is a dominant cycle frequency, and if so what is the dominant cycle frequency. For the purposes of this disclosure, the degree of "domination" of the dominant (stimulation) frequency is related to the capture index.

In the example shown in FIG. 3, the CI was computed as: (Power in range of Stimulation Frequency +/−0.0183 Hz)/(Power from 0.1 to 0.5 Hz). The width of the Numerator in this example is 0.0366 Hz. It is calculated from the stimulation frequency value rounded to the nearest FFT "bin" with the Numerator width of 3 bins below and 3 bins above (6 bins total). The resolution in the frequency domain in this example is 0.0061 Hz/bin. This is termed the "bin width." The choice of +/−3 bins was to account for some or the "bin spreading" that you see when the stimulation frequency is not an exact FFT bin frequency and for some natural variance in the frequency of the entrained breathing. The FFT intervals are fixed by the data sampling rate (400 samples/sec) and the FFT length ($2^{16}$=65,636).

The data sample rate was 400 samples/sec. It is understood that other, lower sampling rates, for example 20 samples/second, may be more suitable for embedded software calculations or other applications. The record length was 65,536 samples (this corresponds to 164.84 seconds). If lower data acquisition sampling rate is used, significantly fewer samples are needed but not likely less than, for example, 1,024 or 2,048. Other record lengths, such as for example 2,3 and 5 minutes were also used successfully. In this example the capture index is calculated as the ratio of the sum of the magnitudes of a frequency band ±3 bins wide (0.0366 Hz), centered around the known stimulation rate and the sum of the magnitudes (or power) from 0.1 to 0.5 Hz.

Other window widths for both the SFB and RFB could be used be used in different embodiments, and the SFB need not be centered on the stimulation frequency. Common to all embodiments the "stimulation frequency band" SFB is narrower than the "respiratory frequency band" (RFB), such as for example <10% of RFB and included within the RFB.

Figure 4:
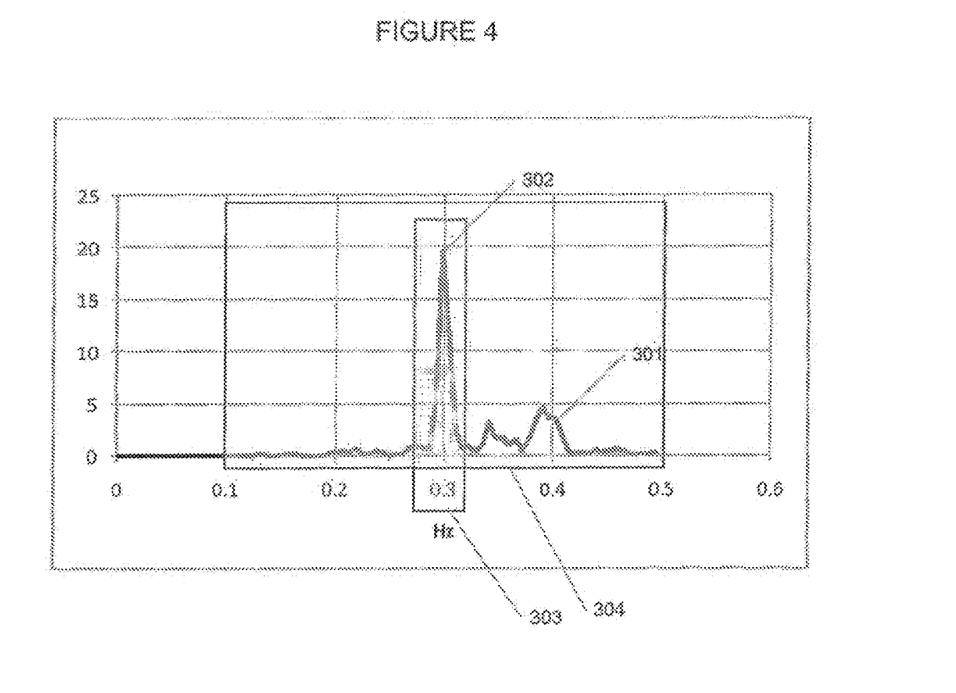
FIG. 4 is a spectral graph of the respiration data presented in FIG. 2.

FIG. 4 is a spectral graph of the respiration data presented in FIG. 2. Stimulation is turned on in this example and applied at the preset frequency of 0.3 Hz as illustrated by the trace 103 on FIG. 2.

It can be seen that the respiratory signal (airflow) power spectrum peak 302 is at the frequency 0.3 Hz that corresponds exactly to the stimulation frequency. Natural respiration power at 0.4 Hz is reflected in a smatter peak 301. It is appreciated that the presence of the natural respiration frequency power in the spectrum can vary depending on the strength of stimulation and the patient's intrinsic respiratory drive. The presence of noticeable respiratory activity at the natural respiratory frequency suggests that the respiratory drive is entrained but still active, i.e. not suppressed or dormant. Power in the SFB 303 in this example represents larger fraction of RFB 304 than in the example illustrated by FIG. 3. Therefore it can be expected that the capture index (SFB/RFB) is also increased significantly. Indeed calculation shows that the capture index increased in this example from 0.24 (FIG. 3) to 0.46 (FIG. 4). Different calculation methods can result in different numbers but the capture index is increased significantly when the patient's respiration is entrained.

Figure 5:
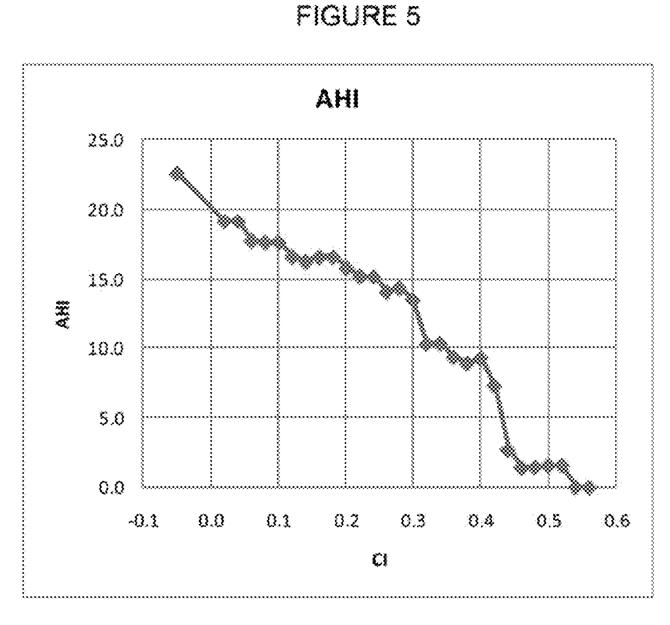
FIG. 5 is a graph of experimental data relating to disordered breathing in a patient treated in accordance with embodiments of the invention.

FIG. 5 is a graph of experimental data relating to disordered breathing in a patient treated in accordance with embodiments of the invention. FIG. 5 illustrates the practical importance of capture indexing for the purpose of restoring normal breathing in the setting of periodic breathing. Severity of periodic breathing is commonly characterized by apnea hypopnea index (AHI). AHI is the total sum of respiratory events (apneas and hypopneas) that occur in one hour. AHI>15 is considered significant and AHI>30 severe and very dangerous. There are known standard clinical methods of calculating AHI during sleep studies using polysomnography (PSG). PSG is a diagnostic test during which a number of physiologic variables are measured and recorded during sleep. The graph of FIG. 5 was obtained by investigators using PSG in a patient suffering from serious periodic breathing while undergoing stimulation therapy in accordance with embodiments of the invention. The patient's AHI is expressed on the Y-axis as a function of capture index on the X-axis. During the experiment stimulation energy (in this case stimulation current) was varied generating different levels of diaphragmic activation and, as a result, different levels of entrainment. Capture index was calculated later using a digitized record of the sleep study and a methodology equivalent to those described in this disclosure.

It can be seen that during time periods when capture index was higher the AHI was reduced. Stimulation resulting in capture indexes higher than 0.5, as calculated in this example, practically eliminated periodic breathing altogether.

It is understood that the use of FFT and the calculation of respiratory spectrum is not the only way to implement the calculation of the capture index. For example, the respiratory waveform can be processed and presented as a series of numbers corresponding to breath lengths. A series representing the last 3-4 minutes of respiratory data can consist, for example, of 60-80 breath lengths. A histogram of breath lengths can be than constructed that represents the frequency distribution of breath lengths. If intrinsic respiration is entrained to a stimulation frequency, the frequency of occurrence of breath lengths corresponding to the wavelength of that frequency will increase. For example if the stimulation frequency is 20/minute the breath length is 3 seconds. As capture and entrainment increase, the breaths approximately 3 seconds long will occur more and more frequently. To compensate for the natural variability, breaths that are, for example, between 2.84 and 3.18 seconds long can be included in the numerator of the capture index calculation. This range of breath lengths corresponds to the +/=0.0183 Hz frequency band used in the spectrum based example described earlier.

The capture index in this method is computed as: (Sum of occupancies of breath lengths in range of Stimulation Frequency +/−selected band)/(Sum of occupancies of all breath lengths in the respiratory range). The respiratory range of breath lengths can be for example from 2 to 10 sec. The 2 to 10 second breath length range corresponds to the 0.1 to 0.5 Hz respiratory frequency.

The histogram based capture verification method is mathematically different from the spectrum based method, but similar in principle. It is based on the assumption that when stimulation entrains respiration, breath lengths of the respiratory signal in the immediate range of the driving frequency will be occurring with significantly higher frequency than those in other respiratory frequency bands. Therefore the Capture Index is still calculated as the ratio of the variance of respiration signal that falls into the narrow band centered on the stimulation frequency to the total variance in the broader respiratory frequency band. Inventors have demonstrated in patients that the value of capture index calculated using the histogram method increased proportionally to the entrainment of respiration by stimulation thus enabling guided therapy and correlated closely with the capture calculated using the spectrum method. It is appreciated that other methods of capture index calculation based on similar principle are possible and will occur to those of skill in the art upon reading this disclosure.

Figure 6:
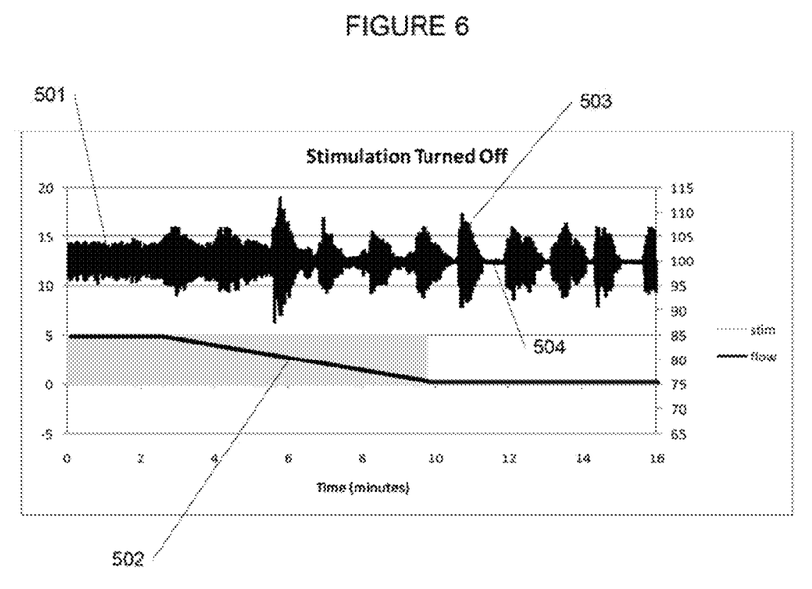
FIG. 6 is a waveform of the respiration and stimulation data associated with a patient therapy in accordance with embodiments of the invention.

FIG. 6 is a waveform of the respiration and stimulation data associated with a patient therapy in accordance with embodiments of the invention. The top trace 501 represents a patient's respiration (airflow). The X-Axis represents 16 minutes of data record and the individual breaths are compressed compared to FIGS. 1 and 2 which showed only one minute of data. During this therapy period the stimulation energy (current) was first gradually reduced and then turned off altogether. The bottom trace 503 represents the stimulation electric current. During the first 3 minutes the current was held constant at approximately 5 mA. Respiration 501 was sufficiently entrained and periodic breathing was not present. During the period between 3 and 10 minutes of the recorded segment the current 503 was gradually reduced. It can be seen that periodic breathing is no longer controlled, and after 10 minutes alternating apneas 504 and hyperpneas 503 indicating the typical pattern of periodic breathing known as Cheyne-Stokes Respiration returns.

Figure 7:
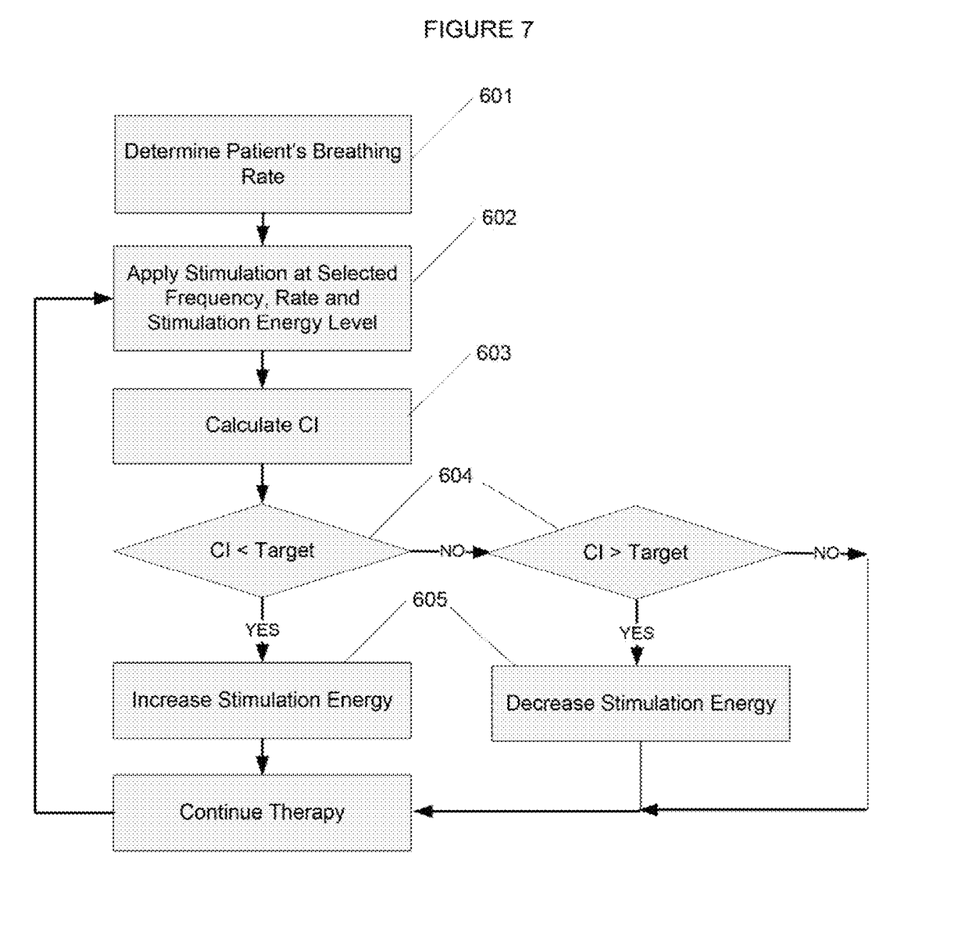
FIG. 7 is a control flowchart in accordance with embodiments of the invention.

FIG. 7 is a control flowchart in accordance with embodiments of the invention. FIG. 7 illustrates one potential method and algorithm that takes advantage of capture indexing to implement and improve disordered breathing therapy. It is understood that the proposed cap index methodology has broad implications for respiratory therapies that use phrenic nerve or diaphragm stimulation and potentially for mechanical ventilation.

One embodiment in accordance with the invention employs a capture index-type calculation embedded in an algorithm in a microprocessor of an implantable pulse generator (IPG) that is capable of adjusting phrenic nerve stimulation energy in response to the calculated capture index. The capture index can be calculated based on 2-3 minutes of history of a respiratory signal, for example transthoracic impedance, and stimulation parameters can be automatically adjusted based on the calculated capture index.

The embedded algorithm of this embodiment is capable of determining the intrinsic resting respiratory rate of the patient 601. This rate can be, for example, between 6 and 40 breaths/minute, but in one targeted population of patients with periodic breathing it is likely between 12 and 30 breaths/minute. The algorithm is capable of applying stimulation pulse trains to the patient's phrenic nerve at a set rate that in some embodiments is somewhat lower than the intrinsic rate 602. It can be, for example, 2-4 breaths lower than the intrinsic rate. Therefore if the patient was determined by the algorithm to be breathing at 20 breaths per minute, the stimulation rate can be automatically set to 16 breaths per minute, for example. After sufficient respiratory signal information is collected by the embedded software (this can be for example 3 minutes of data digitized at 20 samples per second) a capture index can be calculated 603.

Because physiologic conditions such as the patient's position, sleep state, fatigue of the diaphragm and others may influence the response to entrainment, it can be expected that the capture index will not be constant over time. There can be a preset target value of capture index that indicates the desired entrainment. This value can be in the range of 0.2 to 0.8 for example. In accordance with the known art of feedback control engineering, an embedded algorithm can compare the actual capture index with the target 604 and increase stimulation energy if the capture index is below target or reduce it if it is above it 605. The stimulation energy can be adjusted by varying the delivered current, voltage, frequency or pulse duration. For example stimulation current may be increased or decreased in the range between 1 and 10 mA in suitable steps. Alternatively, stimulation pulse duration can be increased or decreased in the range of 100 to 500 μs in suitable steps, for example. A feedback control algorithm can be implemented in the IPG embedded software such as a PI or PID regulator known in the field of control engineering. In the embodiment used by inventors to gather experimental data, the stimulation current was manipulated in steps of 0.1 to 0.5 mA to achieve the desired capture index.

Figure 8:
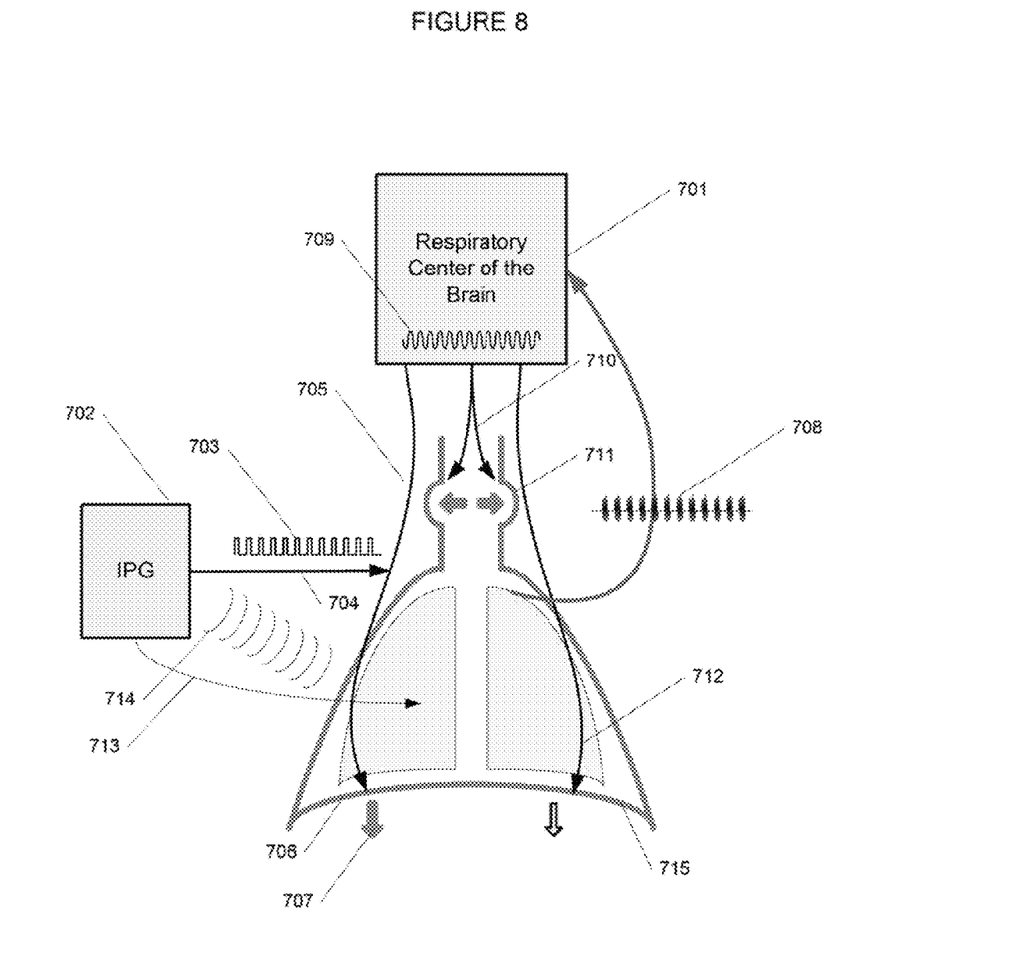
FIG. 8 is a schematic view of a patient and therapy device in accordance with embodiments of the invention.

FIG. 8 is a schematic view of a patient and therapy device in accordance with embodiments of the invention. An implantable pulse generator 702 is programmed to generate stimulation pulse trains 703 at a fixed rate. A right phrenic nerve of the patient 705 innervates the right hemidiaphragm 706. The stimulation pulse trains 703 are delivered to the right phrenic nerve 705 via the electrode lead 704.

Either the phrenic nerve of the hemidiaphragm itself could be stimulated. One or more electrodes could be placed on the diaphragm, adjacent the nerve cuff electrode), intravenously proximate the nerve, or in any other location suitable to provide appropriate stimulation. The etectrode(s) could be connected to an electrical pulse generator using leads or leadless technology. The pulse generator could be implanted within the patient or located externally.

The right phrenic nerve 705 conducts stimulation to the right hemi diaphragm 706, which responds with downward motion 707. The downward motion 707 of the diaphragm results in the inflation of the lungs and activation of stretch receptors within the thoracic cavity. It is believed that periodic stretching generates periodic regular rhythm of neural feedback inputs 708 to the brain 701. Respiratory neurons of the brain are entrained by the neural input 708. The strength of stimulation 703 elicits proportional response from the stimulated head-diaphragm 706. The increased diaphragmic motion accordingly results in the increased periodic regular neural input 708 to the brain 701.

When the signals reach necessary strength, respiratory entrainment is present and the desired fixed and repetitive coupling is established temporarily between stimulation, mechanical inflation of the lungs and neural inspiratory activity in the respiratory control center of the brain. Entrainment may occur at a 1:1 ratio (one mechanical inflation to one neural respiratory effort), but other integral ratios may be seen, as well as occasional aperiodic, chaotic behavior in the transition between different integral ratio entrainment patterns. The 2:1 ratio of two stimulated inflations to one neural respiratory effort is seen commonly together with 1:1 ratio.

The brain responds to entrainment with the regular periodic sequence of respiratory drive 709 that is sent to respiratory muscles of the diaphragm via both right 705 and left 712 phrenic nerves as well as via the airway control nerves 710 to the airway muscles resulting in the desired dilation of the airway 711. The left hemi diaphragm 715 is innervated by the left phrenic nerve 712 that is not stimulated by the IPG and therefore can on occasion exhibit independent behavior in response to the signals coming from the brain 701 and is not directly affected by the IPG 702. It is known that the muscle groups of right and left head diaphragms are innervated separately by right and left phrenic nerves and move independently in response to signals from these nerves. The synchronized respiratory activity of the unstimulated hemi diaphragm is an indication of entrainment as opposed to pacing of respiration.

The IPG 702 can be equipped with additional leads 713 and means to measure respiration such as through transthoracic impedance sensing 714. Software embedded in the IPG programmable logic can respond to the changes in respiration by adjusting the stimulation pulse train rhythm 703. The respiratory sensing 714 can be also used by the IPG logic to set and change the rate of stimulation pulse trains 703 depending on the sensed intrinsic respiratory rate 709.

One skilled in the art will appreciate that the invention can be practiced with embodiments other than those disclosed, The disclosed embodiments are presented for purposes of illustration and not limitation, and the invention is limited only by the claims that follow.

What is claimed is:

1. A method of treating breathing disorders comprising the steps of:
   a. stimulating a phrenic nerve or at a frequency below an intrinsic breathing rate at an intensity sufficient to entrain respiration while leaving intrinsic drive to breathe intact, wherein intrinsic drive to breathe is manifested as periodic activation of airway muscles.

2. The method of claim 1, wherein the stimulation of the phrenic nerve or hemidiaphragm is at the frequency that results in 2:1 entrainment.

3. The method of claim 1, wherein leaving the intrinsic drive to breath intact causes spontaneous breathing of an unstimulated lung.

4. The method of claim 1, wherein leaving the intrinsic drive to breath intact causes breaths interlaced among entrained breaths.

5. The method of claim 1, further including the steps of:
   a. sensing a signal representative of a patient's respiration;

b. determining a frequency distribution from the sensed respiration signal;
c. comparing the frequency distribution of the sensed respiration signal to a target frequency distribution; and
d. adjusting the intensity of the stimulation based on the comparison.

6. The method of claim 5, further including the steps of:
a. measuring the power of an array of sensed respiration signals that fall within a frequency zone related to the stimulation frequency;
b. measuring the total power of sensed respiration signals over a broader frequency zone; and
c. comparing the measured power of signals within the frequency zone related to the stimulation frequency to the measured power of signals of the broader frequency zone.

7. The method of claim 6, wherein the broader frequency zone is between 0 and 0.6 Hertz.

8. The method of claim 6, wherein the broader frequency zone is between 0.1 and 0.5 Hertz.

9. A method of treating breathing disorders comprising the steps of:
a. stimulating a phrenic nerve or diaphragm of a patient at a fixed frequency different from an intrinsic respiration frequency of the patient;
b. sensing a signal representative of the patient's respiration;
c. determining a frequency distribution of the sensed respiration signal;
d. comparing the frequency distribution of the sensed respiration signal to a target frequency distribution;
e. adjusting the intensity of the stimulation based on the comparison of frequency distributions until the stimulation is at an intensity sufficient to entrain respiration while leaving intrinsic drive to breathe intact.

10. The method of claim 9, wherein the stimulation intensity is adjusted by changing the current of the stimulation.

11. The method of claim 10, wherein the stimulation current is increased or decreased in the range between 1 and 10 mA in suitable steps.

12. The method of claim 9, wherein the stimulation signal comprises a series of pluses and the intensity is adjusted by changing the duration of the individual pulses.

13. The method of claim 12, wherein the stimulation pulse duration is increased or decreased in the range of 100 to 500 µs in suitable steps.

* * * * *